United States Patent [19]
Prince et al.

[11] Patent Number: 5,346,488
[45] Date of Patent: Sep. 13, 1994

[54] LASER-INDUCED ABLATION OF ATHEROSCLEROTIC PLAQUE

[75] Inventors: Martin Prince, Cambridge; Allan Oseroff, Brookline; John A. Parrish, Weston, all of Mass.

[73] Assignee: The General Hospital Corporation, Boston, Mass.

[21] Appl. No.: 844,243

[22] Filed: Mar. 2, 1992

Related U.S. Application Data

[63] Continuation of Ser. No. 790,600, Nov. 7, 1991, abandoned, which is a continuation of Ser. No. 720,595, Apr. 8, 1985, abandoned.

[51] Int. Cl.$^5$ .............................................. A61N 5/06
[52] U.S. Cl. .......................................... 606/7; 606/2; 606/3; 606/10; 606/12; 606/15; 607/89
[58] Field of Search ................ 128/395, 397, 398, 898; 606/2, 3, 7, 10–19; 607/89, 88

[56] References Cited

U.S. PATENT DOCUMENTS 3,769,963  11/1973  Goldman et al. ...................... 606/3
4,669,467  6/1987  Willett et al. .......................... 606/15

OTHER PUBLICATIONS

"Selective Photo-Removal of Athermatous Arterial Obstructions" by Prince Thesis Mar. 1985.
"Fluorescence Bronchoscopy for Detection of Lung Cancer" by Docrin et al; Chest, 76:1; Jul. 1979 pp. 27–32.
"The Infiltration of Carotenoids into Human Atheromas and Xanthomas" by Blankenhorn; An Int Med; vol. 53, Nov. 1960, pp. 944–954.

*Primary Examiner*—David M. Shay
*Attorney, Agent, or Firm*—Allegretti & Witcoff, Ltd.

[57] ABSTRACT

A method of ablating atherosclerotic plaque by means of short-duration laser light pulses. A carotenoid, such as beta-carotene, is preferably administered to the patient by injection or ingestion prior to exposing the plaque with laser light. Research data obtained by analysis of the absorption characteristics of plaque and the healthy arterial tissue reveals that the plaque may be selectively ablated without damaging the surrounding normal tissue by illuminating the plaque with laser light having a wavelength of about 430 to about 510 nanometers such that the relative absorption coefficient exhibited by the plaque is more than 1.5 times the absorption coefficient of the arterial tissue. Short duration laser light pulses preferably illuminate the plaque for less than the thermal relaxation time of the volume of exposed material. The intensity of the laser light is preferably in the range from about 1 to about 9 joules/cm$^2$ in order to ablate the plaque without endangering the surrounding tissue. The carotenoid administered to the patient enhances the absorption coefficient of the plaque to facilitate ablation and additionally facilitates the detection of the plaque.

31 Claims, 3 Drawing Sheets

LASER-INDUCED ABLATION OF ATHEROSCLEROTIC PLAQUE

RELATED APPLICATIONS

This is a continuation of application Ser. No. 07/790,600 filed on Nov. 7, 1991, now abandoned, which is a continuation of Ser. No. 06/720,595 filed on Apr. 8, 1985, now abandoned.

BACKGROUND OF THE INVENTION

This invention relates to the ablation of atherosclerotic plaques in human patients using lasers.

Such ablation has been carried out using a variety of lasers, e.g., argon lasers, at various wavelengths, e.g., 514 nm (for argon lasers). The technique typically involves the use of a flexible optical fiber associated with the laser, as described, e.g., in Choy U.S. Pat. No. 4,207,874, hereby incorporated by reference. In known techniques, the plaque is first visualized, either by angiography or using a coherent fiber optic bundle built into the laser catheter, and the ablating laser is then aimed and "fired" at the plaque.

There have been some attempts to improve selectivity in the absorption of laser light by plaques, compared to surrounding tissues, by selectively staining the plaque with, e.g., hematoporphyrin (Spears et al. (1983) J. Clin Invest. 71, 39–399). Hematoporphyrin is a photosensitizing agent which, when exposed to laser light, may bring about the photochemical destruction of the plaque.

SUMMARY OF THE INVENTION

In general, the invention features an improved laser-induced plaque ablation method, involving exposing the plaque to pulsed laser light characterized in that its wavelength is at value at which the ratio of Kubelka-Murk absorption coefficients of the plaque to normal human aortic endothelium is at least 1.5:1, more preferably 2:1 or higher.

In preferred embodiments, the laser light is further characterized in that it is delivered to the plaque in a series of pulses of duration less than the thermal relaxation time of the volume of tissue defined by the diameter of the laser beam within the tissue and the depth at which 67% of the incident light of the laser has been absorbed; a chromophore preferentially taken up by plaques is administered, orally or intravenously, to the patient prior to exposure to the laser light; the administered chromophore is a carotenoid such as β-carotene; the wavelength of the laser light as 440–480 nm, more preferably about 460 nm; and administration of β-carotene is oral and is carried out at least once daily for at least two days, and more preferably at least one week, prior to the exposure to the laser light, at a dosage of between 100 mg and 5,000 mg per day, and preferably at least 300 mg per day.

The invention provides selective absorbance of laser energy by plaques compared to surrounding tissue, by virtue of the use of a laser tuned to the absorbance wavelength of the mixture of chromophores (primarily carotenoids) naturally present in plaque in greater concentrations than in surrounding healthy tissues, to which thermal laser-induced damage is to be minimized. This selective absorption effect can be enhanced by the administration of a chromophore which is selectively taken up by plaque, as carotenoids are known to be.

The invention also provides for selective heating of plaques, compared to surrounding tissues, by employing very short pulses, which prevent heat from damaging healthy tissues adjacent to the target plaque area.

Other features and advantages will be apparent from the following description of the preferred embodiments thereof, and from the claims.

DESCRIPTION OF THE PREFERRED EMBODIMENTS

The drawings will first be described.

DRAWINGS

ABSORPTION AND WAVELENGTH

Figure 1:
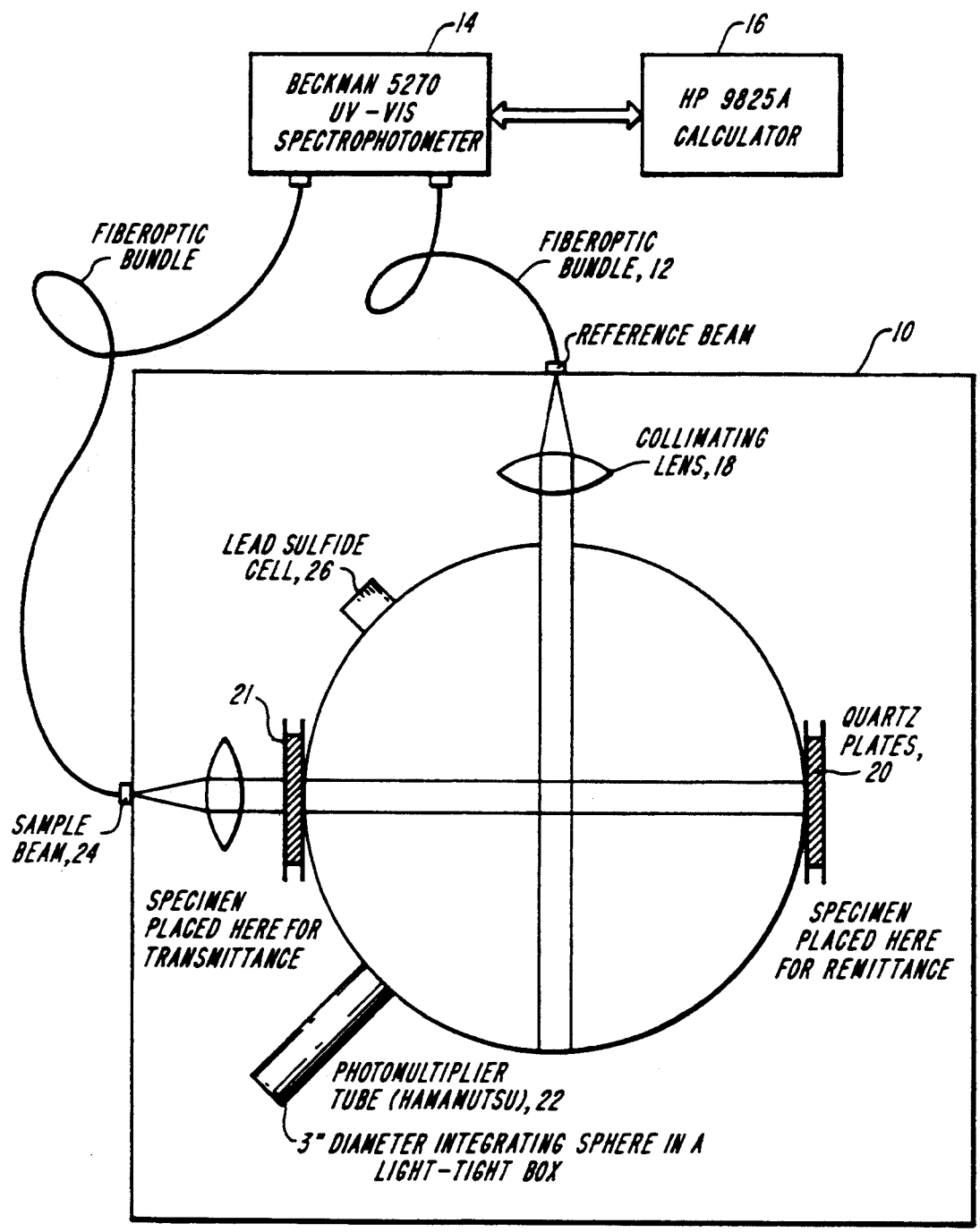
FIG. 1 is a diagrammatic representation of apparatus used to determine the wavelength of tissue absorption.

The first step in the plaque ablation method of the invention is to select a wavelength at which the plaque:-normal aorta Kubelka-Munk absorption coefficent is at least 1.5:1. This difference in absorption coefficients (seen at about 460 nm in patients not administered supplemental chromophore) results from the preferential accumulation in plaque of dietary carotenoids.

Where a chromophore is administered to the patient prior to ablation, the wavelength employed will reflect the concommitant change in the composition of the plaque. For example, administration of a chromophore, e.g., capsanthin, which absorbs at a wavelength above 460 nm will bring about some increase in the optimal wavelength. However, because carotenoids are already present in the plaque, the administration of a chromophore absorbing above or below the pre-administration optimum will generally result in an optimal wavelength somewhere between the absorption maximum of the administered chromophore, .and the pre-administration optimum. The absorption maxima of ten suitable carotenoids known to exist in humans and, in some instances, in foods, are given in the table below.

| carotenoid | absorption maxima in light petroleum (nm) |
|---|---|
| lycopene | 446,472,505 |
| beta-carotene | 425,451,480 |
| canthaxanthin | 466 |
| alpha carotene | 422,444,480 |
| zeta carotene | 378,400,425 |
| lutein | 420,447,477 |
| cryptoxanthin | 425,451,483 |
| zeaxanthin | 423,451,483 |
| capsanthin | 474-475,504 |
| capsorubin | 444,474,506 |

The Kubelka-Murk absorbance coefficients of plaque and normal aortic tissue are measured by conventional techniques, as is explained in more detail below.

CHROMOPHORE ADMINISTRATION

The amount, duration, and mode of administration of the chromophore will depend on its properties, e.g., toxicity and affinity for plaque. Some carotenoids are naturally present in high concentrations in foods such as carrots and tomatoes, and administration of these could be achieved at least in part by daily ingestion of such foods. The chromophore can also be administered, orally, admixed with a pharmaceutically acceptable carrier substance, in a pill or liquid, or can be administered intravenously or intraperitoneally.

It is particularly useful to employ a chromophore which, in addition to being preferentially accumulated in plaque, fluoresces, facilitating detection and laser aiming. Carotenoids, for example, advantageously fluoresces when excited at 460 nm.

PULSE DURATION

As mentioned above, the pulse duration used is related to the thermal relaxation time t of the volume of tissue defined by the diameter of the laser beam within the tissue and the depth at which 67% of the incident light of the laser has been absorbed; the relaxation time is the time it takes for the temperature increase ($\Delta T$) caused by a pulse of light of a duration approaching zero to decrease by one-half at the surface of that tissue volume after the pulse has ceased.

Thermal relaxation time t is roughly approximated by:

$$t = \frac{d^2}{2K}$$

where d, expressed in cm, is the smaller of the diameter of the irradiated volume (conventionally referred to as "D") and the depth at which 67% of the incident light has been absorbed (conventionally referred to as "d"). K is the thermal difussivity, in $cm^2$/sec.; K is approximately 0.0013, for water. It should be emphasized that this method of calculating t is given for convenience only; where reference is made herein to the relationship between pulse duration and t, actual t, as defined earlier in terms of a one-half decrease in $\Delta T$, is intended.

PULSE FLUENCE

The fluence (Joules/$cm^2$) of the laser light should be sufficiently high to cause heating of the target plaque, at the wavelength and pulse duration employed, to a temperature at which a substantial portion of the plaque is burned away, and not so high as to cause unacceptable damage to surrounding healthy tissue. The requisite fluence range varies with the diameter of the optical fiber used in conjunction with the laser. Generally, a fluence of 2-10 J/$cm^2$ is preferred for a 1 mm diameter optical fiber, while smaller diameter fibers will require higher fluences to compensate for scattering losses at the periphery of the illustrated volume.

For fluorescence detection, a lower, non-burning intensity, e.g., about 1 milliwatt, is used in a pulsing or continuous mode to excite fluorescence.

Laser and Associated Apparatus

Any laser which can deliver pulses of the desired intensity, duration, and wavelength can be used. A preferred laser is a flashlamp pumped pulse dye laser. The fiber optic bundles and auxiliary apparatus by which laser light is delivered to the plaques can be of any conventional configuration, e.g., as described in Choy, id. A second fiber optic bundle can be used for plaque detection, and if fluorescence of a plaque-associated carotenoid is to be employed in detection, excitation can be achieved by means of a third optic bundle, or by use of the ablation bundle in an excitation mode.

A particular plaque ablation procedure was carried out as follows.

KUBELKA-MURK ABSORBANCE COEFFICIENTS

Absorbance coefficients were determined by measuring remittance and transmittance of normal aortic endothelium and aortic plaque, essentially by the integrating sphere technique described in Anderson et al. (1979) Proc. Symp. Bioengineer and the Skin, Cardiff, Wales (MTP Press, London).

The procedure was carried out using the apparatus shown in FIG. 1, including 7.5 cm diameter barium sulfate coated integrating sphere 10, connected by 2 mm diameter quartz fiber optic bundles 12 to Beckman 5270 double beam spectrophotometer 14, which is interfaced with Hewlett Packard 9825A computer 16 for digital data acquisition and analysis. Freshly coated barium sulfate plates (not shown) were used as 100% remittance standards. The apparatus further included collimating lens 18, for providing a collimating light beam to illuminate a 5 mm diameter region of the tissue; quartz sample-holding plates 20 and 21; photomultiplier tube 22; beam source 24; fiber optic bundle 26, connecting beam source 24 with spectrophotometer 14; and lead sulfide cell 26.

To use the apparatus of FIG. 1 to determine absorption coefficients, cadaveric specimens of human aorta were obtained less than 48 hours post mortem. Optical measurements were made on soft, yellow, raised plaques in which the outer portion of the media and adventicia had been stripped by blunt dissection. Specimens were 0.2 to 2 mm thick. The specimens were mounted sandwiched between polished quartz plates 20 (for remittance measurement) or 21 (for transmittance measurement), and the tissue surface irregularities filled in with saline to replace the irregular air-tissue interface with a smooth air-quartz interface. The air-quartz interface had a consistent and predictable remittance that was measured and subtracted from the tissue remittance measurement.

The tissue-quartz plate sandwiches were placed on the integrating sphere apparatus of FIG. 1; remittance and transmittance measured as in Anderson et al., id, and Kubelka-Murk absorption coefficients calculated as described therein.

Figure 3:
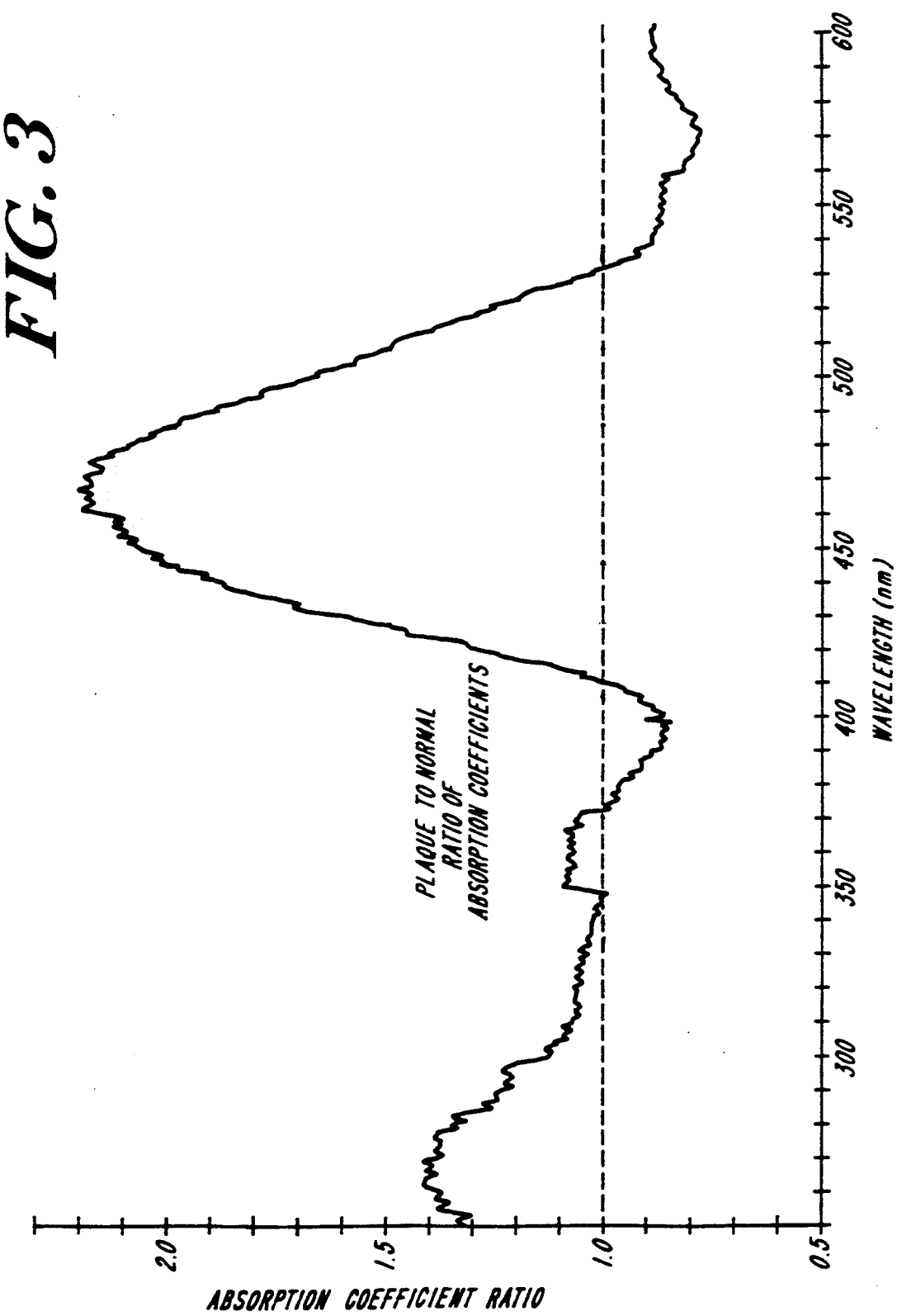
FIG. 3 is a graph showing ratios of absorption coefficients for normal human aortic endothelium and aortic plaque over a range of wavelengths.

The results are given in FIG. 3, expressed as the plaque to normal ratio. As shown in FIG. 3, the ratio is highest between 440 and 480 nm, with a peak at 460 nm.

PLAQUE ABLATION

Figure 2:
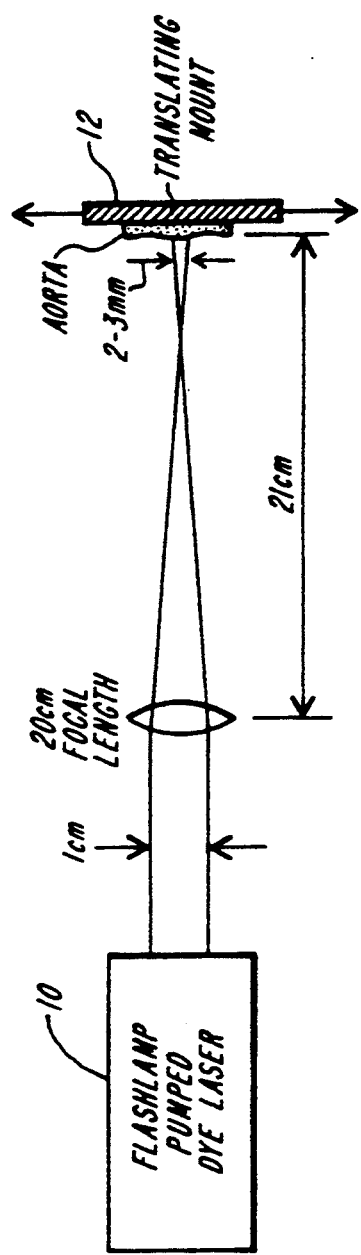
FIG. 2 is a diagrammatic representation of a laser and associated apparatus used to demonstrate selective plaque ablation according to the invention.

Ablation of aortic plaques of cadavers was carried out using the apparatus of FIG. 2, including Candella SLL 500 Coaxial Flashlamp pumped dye laser 10, translating tissue mount 12, and a 40% output coupler (not shown).

The laser generated 1 microsecond pulses with energies up to 2 joules at 459 to 470 run with coumarin 445 laser dye (Exciton # C445), $1.5 \times 10^{-4}$ molar in 50% methanol and 50% distilled water. Laser wavelength output was measured with a high intensity monochrometer (Bausch Lomb # 33-86-76) and the pulse width characterized with an ultrafast silicon photodiode (EG&G FND 100Q) reverse biased by 90 volts. The laser mirrors were adjusted until output burn patterns on polaroid film were circular. The 1 cm diameter light beam coming out of the laser was focused with a 20 cm focal length quartz lens to form a 2–3 mm diameter spot on the specimen. The specimen could then be translated across the laser beam to give an identical radiation dose to several normal and atheromatous regions of cadaver aorta, obtained as before. Specimens were irradiated, photographed fresh, fixed in formalin, bisected through the rows of irradiation sites, and photographed in cross section.

At 400 mJ per pulse, 20 pulses formed an obvious crater in plaque but caused only slight browning in, and no removal of, adjacent normal tissue. Plaque required 3.2–7.9 $J/cm^2$ for removal and normal aortic tissue required 9.7–20.5 $J/cm^2$. In general the yellower and softer atheromas had the lowest thresholds while hard and/or pale atheromas had higher threshold fluences.

Other embodiments are within the following claims.

We claim:

1. A method of enhancing absorption of light by atherosclerotic plaque in a human patient to improve discrimination of said atherosclerotic plaque from surrounding tissue by light, comprising, the steps of:
   administering a carotenoid to said human patient whereby at least a portion of said carotenoid accumulates in said atherosclerotic plaque thereby altering said atherosclerotic plaque's composition.

2. The method of claim 1 wherein said step of administering said carotenoid comprises administering by injection.

3. The method of claim 2 wherein said step of administering said carotenoid comprises injecting said carotenoid at least once daily.

4. The method of claim 3 wherein said said step of administering carotenoid comprises injecting said carotenoid at least once daily for at least one week prior to exposure to said light.

5. The method of claim 1 wherein said step of administering said carotenoid comprises administering said carotenoid by injection or ingestion.

6. The method of claim 5 wherein said carotenoid is administered at least once daily.

7. The method of claim 5 wherein said step of administering said carotenoid comprises administering said carotenoid at least once daily for at least one week prior to exposure to said light.

8. A method of enhancing absorption of light by atherosclerotic plaque in a human patient to improve elimination of said atherosclerotic plaque by light, comprising, the steps of:
   administering a carotenoid to said human patient whereby at least a portion of said carotenoid accumulates in said atherosclerotic plaque thereby altering said atherosclerotic plaque's composition.

9. The method of claim 8 wherein said step of administering said carotenoid comprises administering said carotenoid by injection.

10. The method of claim 9 wherein said step of administering said carotenoid comprises injecting said carotenoid at least once daily.

11. The method of claim 10 wherein said step of administering said carotenoid is injected at least once daily for at least one week prior to the exposure to said light.

12. The method of claim 8 wherein said step of administering said carotenoid comprises administering said carotenoid by ingestion.

13. The method of claim 12 wherein said step of administering said carotenoid comprises administering said carotenoid at least once daily.

14. The method of claim 13 wherein said step of administering said carotenoid comprises administering said carotenoid at least once daily for at least one week prior to the exposure to said light.

15. A method of ablating atherosclerotic plaque within a blood vessel in a human patient comprising,
   administering to said patient a carotenoid which is selectively taken up by said atherosclerotic plaque; and
   exposing said atherosclerotic plaque to pulsed laser light having:
   a wavelength defined by a ratio of absorption coefficients of said atherosclerotic plaque to normal human aortic endothelium being at least 1.5:1,
   a pulse duration defined as being less than a thermal relaxation time of the atherosclerotic plaque exposed to said pulsed laser light, and
   a beam intensity defined as being capable of heating said atherosclerotic plaque, at the wavelength and pulse duration employed, to effect ablation of said atherosclerotic plaque without removal of surrounding normal human aortic endothelium.

16. The method of claim 15 wherein said step of administering said carotenoid comprises administering $\beta$-carotene.

17. The method of claim 16 wherein each said step of administering $\beta$-carotene comprises administering a dosage of between 100 mg and 5,000 mg per day.

18. The method of claim 17 wherein said step of administering includes administering a dosage of at least 300 mg per day.

19. The method of claim 15 wherein said step of administering includes intravenously administrating said carotenoid.

20. The method of claim 15 wherein said administering step includes carrying out said administering step and is carried out at least once daily for at least two days prior to said exposure.

21. The method of claim 20 wherein said step of administrating includes intravenously administrating said carotenoid at least once daily for at least one week prior to said exposure to said laser light.

22. A method of ablating atherosclerotic plaque in a human patient, comprising, in combination, the steps of:
   increasing an absorption coefficient of said atherosclerotic plaque for pulsed laser light having a wavelength within a predetermined range by introducing a carotenoid into the human patient's bloodstream wherein said carotenoid preferentially accumulates in said atherosclerotic plaque;
   generating multiple pulses of laser light having a wavelength defined as being within said predetermined range, having a pulse duration defined as being less than a thermal relaxation time of the atherosclerotic plaque exposed to said multiple pulses of laser light, and having a pulse fluence defined as being within a range from 1 to 9 joules per square centimeter, such that said multiple pulses of laser light effects ablation of said atherosclerotic plaque as altered by the carotenoid accumulated in said atherosclerotic plaque;
   exposing said atherosclerotic plaque to said multiple pulses of laser light.

23. The method of claim 22 wherein said step of administering carotenoid comprises administering beta-carotene.

24. The method of claim 22 wherein said step of generating multiple pulses of laser light comprises generating said pulse fluence of said multiple pulses of laser light to be within a range from 1 to 5 joules per square centimeter.

25. The method of claim 22 wherein said step of generating multiple pulses of laser light comprises generating said pulse duration to be less than 1/10th of the thermal relaxation time.

26. The method of claim 22 wherein said step of generating multiple pules of laser light comprises generating said pulse duration of said laser light to be about 1 microsecond.

27. The method of claim 22 wherein said step of generating multiple pules of laser light comprises generating said predetermined range of wavelengths to be within a range from 430 to 510 nanometers.

28. The method of claim 22 further comprising detecting the atherosclerotic plaque by exposing said atherosclerotic plaque to pulsed laser light having a wavelength and a pulse fluence selected to detect said atherosclerotic plaque and wherein, once detected, the atherosclerotic plaque is exposed to said pulsed laser light wherein said pulsed laser light substantially ablates said atherosclerotic plaque.

29. The method of claim 22 wherein said step of introducing said carotenoid comprises introducing by ingestion or injection.

30. The method of claim 29 wherein said carotenoid comprises introducing said carotenoid at least once a day prior to exposing said atherosclerotic plaque to said pulsed laser light.

31. The method of claim 30 wherein said step of inducing carotenoid comprises introducing beta-carotene.

* * * * *